United States Patent [19]

Fischer

[11] Plant 5,063

[45] Jun. 28, 1983

[54] AFRICAN VIOLET NAMED JOYCE

[75] Inventor: Arnold W. Fischer, Hanover, Fed. Rep. of Germany

[73] Assignee: Pan-American Plant Company, Parrish, Fla.

[21] Appl. No.: 268,099

[22] Filed: May 28, 1981

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Chas. W. Rummler

[57] ABSTRACT

A new African Violet cultivar distinguished by its profuse production of medium sized, wine-red flowers of good substance and keeping quality and by its vigorous and strong growth habit which produces a compact plant of rosette form.

4 Drawing Figures

BACKGROUND OF THE NEW PLANT

This plant originated as a seedling of unknown parentage growing among greenhouse plants maintained for breeding purposes at Fallbrook, Calif., and was discovered by me in 1977. The strong and vigorous rosette form of growth and its pleasing red flowers led me to select this plant for propagation and further study, reproduction of the selected plant being done by means of cuttings at Fallbrook and carried on through successive generations which demonstrated that this new variety of violet had excellent horticultural characteristics. This new variety has retained its novel features from generation to generation and they appear to be firmly fixed.

DESCRIPTION OF THE DRAWINGS

This new violet plant is illustrated by the accompanying drawings, of which sheet 1 is a full color photographic view of a potted plant in full bloom, sheet 2 is a photographic print showing full face views of flowers of this variety which has been hand-painted to show the true flower colors, and sheets 3 and 4 are prints of machine copies of the front and back sides, respectively, of typical leaves of this plant.

DESCRIPTION OF THE NEW PLANT

The following is a detailed description of my violet plant based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African Violet.

Form: Compact and rosette shaped.
Growth: Strong and vigorous.
Foliage: Abundant with about 25 leaves.
- *Size of leaf.*—Width — Various, from insignificant to 65 mm. Length — From insignificant to about 70 mm.
- *Shape.*—Oval with acute tip, cordate base, and repand type of margin.
- *Texture.*—Pubescent.

- *Aspect.*—Glossy.
- *Color.*—Upper Side — 137A. Under Side — 66D.
- *Ribs and veins.*—Pinnate and very prominent on the under side of the leaf.
- *Petioles.*—Length — Insignificant to about 75 mm.

THE BUD

Form: Globular.
Size: Average with various lengths and diameters at time of opening.
Opening rate: Typical violet.
Color of petals:
- *When sepals first divide.*—65A.
- *When petals begin to unfurl.*—72A.

Sepals:
- *Number.*—5.
- *Shape.*—Lanceolate, branched and hooded over the bud. When the flowers open, the sepals become flat.
- *Color.*—Inside — 199A. Outside — 199A.
- *Striae.*—None.

Calyx:
- *Size.*—Small, splits to star shape.
- *Aspect.*—Hairy.

Peduncle:
- *Character.*—Rigid and erect.
- *Aspect.*—Hairy.
- *Length.*—From insignificant to about 85 mm.
- *Color.*—199C.

THE FLOWER

Blooming habit: Intermittent and profuse.
Flowers:
- *Borne.*—As a cyme.
- *Size.*—Medium, flat and about 30 to 38 mm. in diameter.
- *Shape.*—Cup-shaped when bloom first opens and becoming flat as the bloom matures.

Petalage:
- *Number.*—Five.
- *Arrangement.*—Sympetalous.
- *Form.*—Zygomorphic and rotate with rounded apex and slightly undulating margin.
- *Texture.*—Soft.
- *Aspect.*—Satiny.
- *Color.*—Face Side — 72A. Reverse Side — 74D.

Peduncle:
- *Character.*—Strong and upright.

*Length.*—From insignificant to about 85 mm.
*Color.*—199C.

Persistence: The flower hangs on and dries.
Fragrance: None.
Lasting quality: 10 to 20 days on the plant.

REPRODUCTIVE ORGANS

Stamens:

*Anthers.*—Five in number and in monadelphous arrangement. Size: About 3 mm. square. Color: Yellow.

*Filaments.*—About 3 mm. long. Color: Whitish yellow.

*Pollen.*—Color — Yellow.

Pistils:

*Number.*—One.
*Styles.*—Length: About 5 mm. Color: 72A.
*Stigma.*—Color — Whitish.

Ovaries: Hypogynous and tomentose.

This new variety of African Violet plant has excellent growth characteristics and a profuse production of blooms borne in a bouquet above medium green foliage, and the single wine-red flowers are characterized by very good substance and keeping quality.

I claim:

1. A new variety of African Violet, substantially as herein shown and described, characterized by its profuse production of medium sized flowers, bloomed intermittently and borne on strong, upright stems.

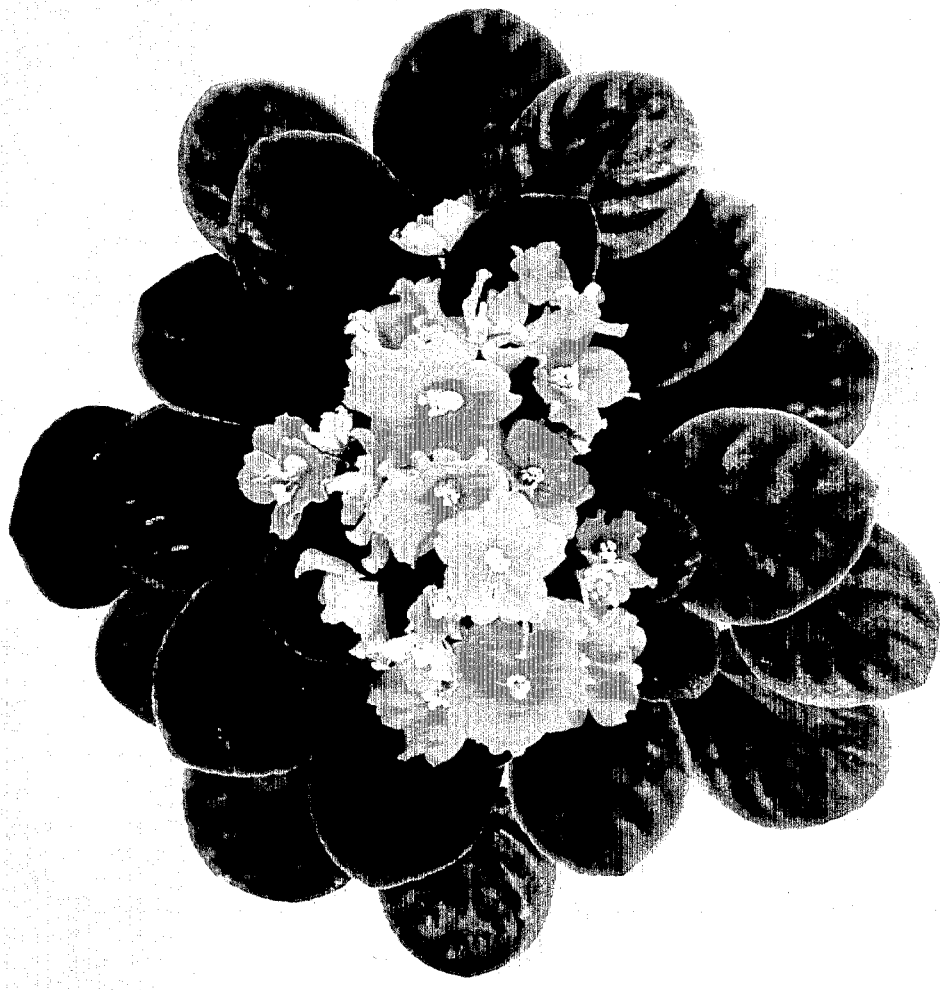

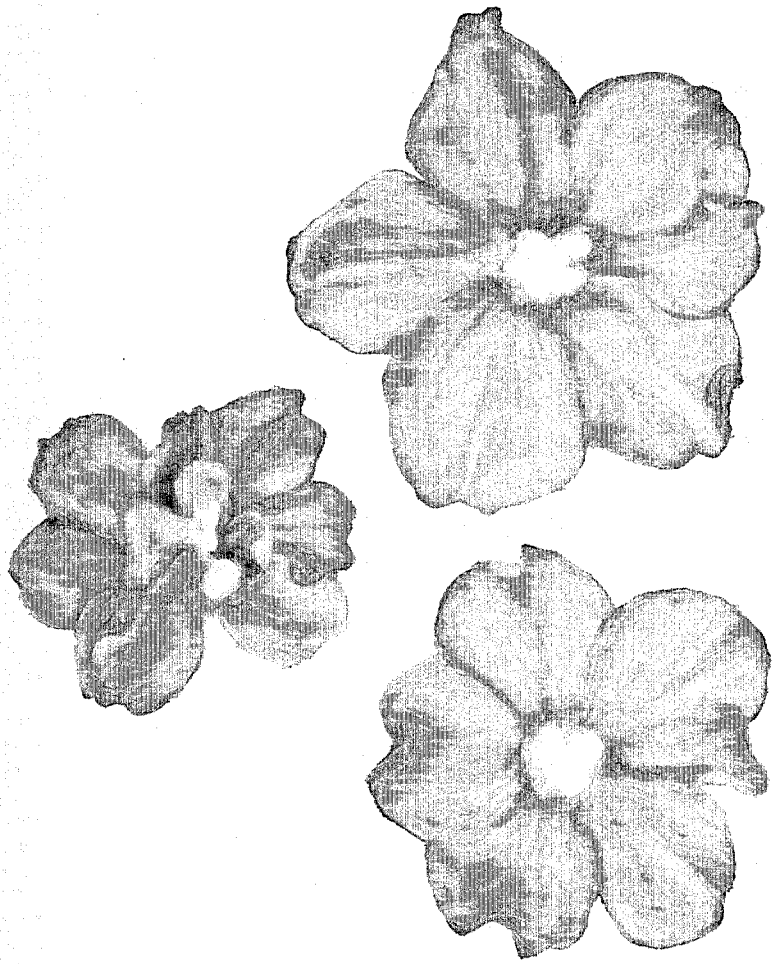

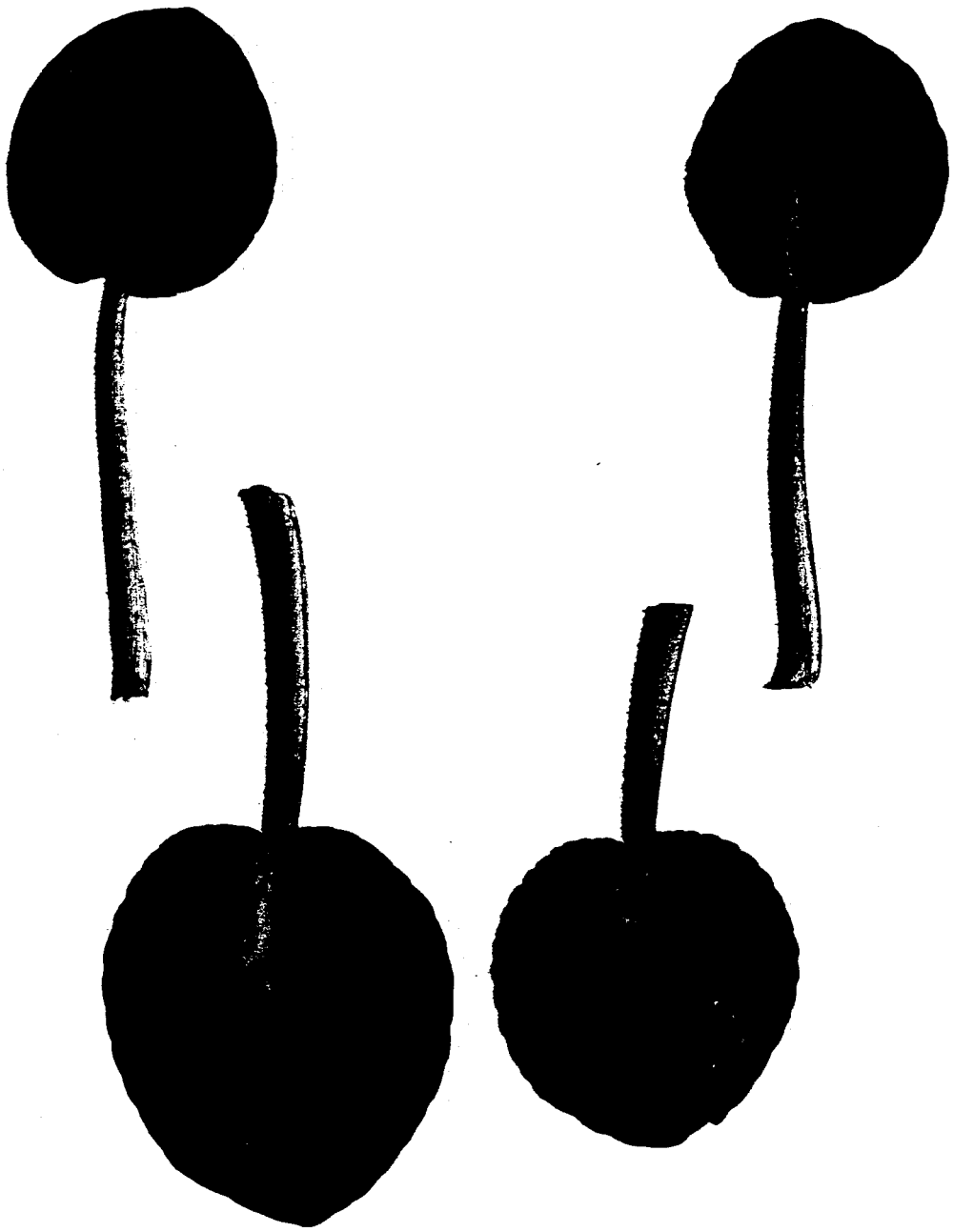

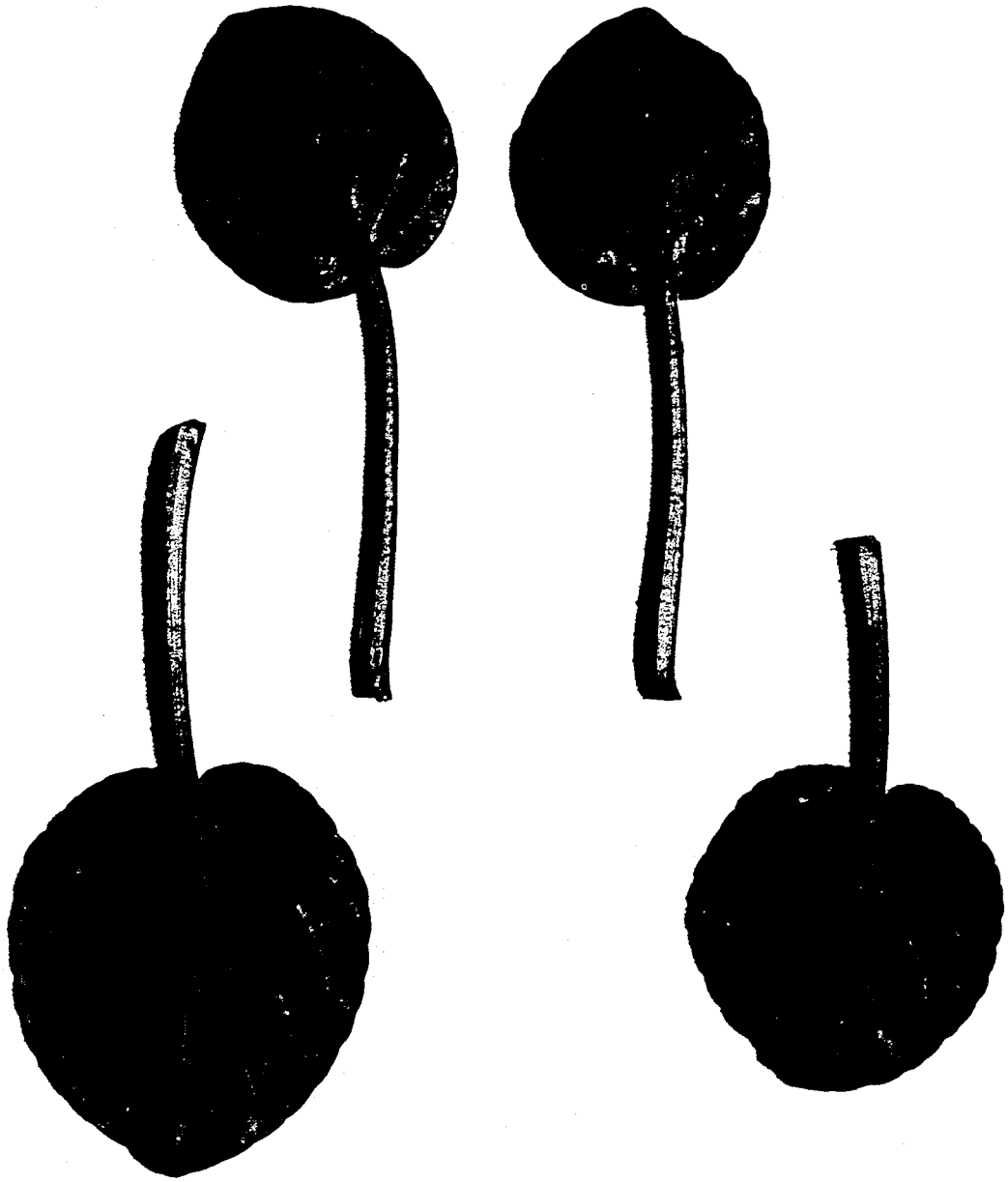

* * * * *